United States Patent
Stroup (10) Patent No.: US 6,742,246 B2
(45) Date of Patent: Jun. 1, 2004

(54) SYSTEMS FOR ASSEMBLING INJECTION DEVICES

(75) Inventor: David Karl Stroup, El Cajon, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 108 days.

(21) Appl. No.: 10/057,380

(22) Filed: Jan. 23, 2002

(65) Prior Publication Data

US 2003/0135978 A1 Jul. 24, 2003

(51) Int. Cl.[7] .................................................. B23P 19/00
(52) U.S. Cl. ........................ 29/823; 29/822; 29/281.1; 29/33 T; 29/777; 198/608; 198/612
(58) Field of Search ........................ 29/429, 464, 525, 29/559, 33 K, 33 T, 709, 722, 822, 823, 824, 281.1, 281.5, 777; 198/604, 608, 612

(56) References Cited

U.S. PATENT DOCUMENTS

| | | | | |
|---|---|---|---|---|
| 1,896,386 A | * | 2/1933 | Williams | 198/589 |
| 2,829,757 A | * | 4/1958 | Breeback | 198/434 |
| 3,096,575 A | * | 7/1963 | Cook | 29/429 |
| 3,360,099 A | * | 12/1967 | Barr | 198/463.3 |
| 3,551,993 A | * | 1/1971 | Cassai et al. | 29/429 |
| 3,623,210 A | * | 11/1971 | Shields | 29/429 |
| 3,708,945 A | * | 1/1973 | Klettke | 53/471 |
| 3,973,313 A | * | 8/1976 | Hunter | 29/564.2 |
| 3,994,059 A | * | 11/1976 | Watson | 29/429 |
| 4,003,123 A | * | 1/1977 | Duke | 29/429 |
| 4,064,987 A | * | 12/1977 | Rowan | 198/604 |
| 4,070,756 A | * | 1/1978 | Shields | 29/809 |
| 4,741,090 A | * | 5/1988 | Monnier | 29/464 |
| 5,031,297 A | * | 7/1991 | Nelson | 29/446 |
| 5,134,763 A | * | 8/1992 | Schulz et al. | 29/91 |
| 5,146,666 A | * | 9/1992 | Babbitt et al. | 29/429 |
| 5,539,981 A | * | 7/1996 | Burcham et al. | 29/888.061 |
| 6,032,348 A | * | 3/2000 | Haas et al. | 29/434 |
| 6,109,426 A | * | 8/2000 | Messer, III | 198/817 |

* cited by examiner

*Primary Examiner*—Peter Vo
*Assistant Examiner*—Essama Omgba
(74) *Attorney, Agent, or Firm*—Orrick, Herrington & Sutcliff LLP (57) ABSTRACT

Apparatus for assembling injection devices includes first and second pairs of shafts spaced apart from one another and defining axes extending parallel to a first inclined axis. The shafts include grooves extending helically between ends of the shafts, the helical grooves together defining passages extending vertically between the shafts. The shafts are rotated about their axes such that the passages move between first and second ends of the shafts. Syringes are introduced into successive passages to carry the syringes downwardly along the inclined axis between the first and second ends of the shafts while maintaining the syringes oriented vertically and spaced apart. Guards are carried along a horizontal axis that converges with the inclined axis at a convergence region. The guards are spaced apart and suspended vertically below corresponding syringes such that the syringes are received in successive guards at the convergence region.

18 Claims, 9 Drawing Sheets

SYSTEMS FOR ASSEMBLING INJECTION DEVICES

FIELD OF THE INVENTION

The present invention relates generally to apparatus and methods for assembling injection devices, and more particularly to apparatus and methods for loading syringes into adapters or guard devices including shields for covering needles of the syringes after use.

BACKGROUND

Medication is often dispensed using a medical cartridge, such as a syringe, having a barrel with a needle extending from one end and a plunger slidably inserted into the other end. Such cartridges are often referred to as "pre-filled syringes" because they contain a specific dosage or volume of medication when they are initially provided, as compared to conventional syringes, which are furnished empty and filled by the user before making an injection.

Alternatively, a medical cartridge may be used, such as an ampoule or vial, that includes a penetrable seal instead of a needle on one end of the barrel, and/or a piston rather than a plunger on the other end. Such medical cartridges are generally inserted into an adapter that includes a hollow body configured to hold the cartridge, a plunger to engage and move the piston in the cartridge, and/or a double-ended needle to penetrate the seal and communicate with the interior of the barrel.

Syringe guards have been suggested that include a body within which a syringe may be received, and a shield that is slidable with respect to the body to cover the needle. For example, U.S. Pat. Nos. 6,030,366, 6,159,183, and 6,171,283, assigned to the assignee of the present application, disclose guards that include a body having an open proximal end for inserting a syringe into a cavity within the body. The body includes a plurality of detents for engaging a flange on the syringe to substantially permanently encapsulate the syringe in the body.

The body includes a distal end with an opening through which a needle on the syringe may extend once received in the body. A shield is slidable over the body between retracted and extended positions to expose and cover the needle, respectively. With the shield in the retracted position and the needle exposed, an injection may be made, and then the shield may be manually advanced to the extended position. In the extended position, cooperating detents on the body and shield lock together, thereby preventing reuse of the needle, reducing the risk of accidental needle sticks, and/or facilitating disposal of the syringe.

Such a guard may be provided to a user without a syringe or medical cartridge. The user may insert a syringe into the guard immediately before use, perform an injection, and advance or otherwise activate a shield on the guard. Such user loading, however, involves extra handling of the syringe, and/or may result in improper insertion of the syringe into the guard.

Accordingly, apparatus and methods for assembling medical cartridges into adapters, such as syringes into guards, to provide pre-loaded injection devices ready for use would be considered useful.

SUMMARY OF THE INVENTION

The present invention is directed to apparatus and methods for assembling injection devices, including a syringe or other medical cartridge received into an adapter that may or may not include a shield device. More particularly, the present invention is directed to apparatus and methods for assembling syringes into bodies of guard devices including shields for covering needles of the syringes after use.

In accordance with one aspect of the present invention, an apparatus is provided for assembling an injection device including a medical cartridge and an adapter including a body for receiving the medical cartridge in an open end thereof. A pair of first shafts may be disposed adjacent one another, each first shaft including a helical groove therein extending between first and second ends of the first shaft. One or more second shafts, and preferably a pair of second shafts, may be spaced apart a predetermined distance from the pair of first shafts, the first and second shafts extending substantially parallel to a first longitudinal axis. Each second shaft may include a helical groove therein extending between first and second ends of the second shaft.

The helical grooves in the first and second shafts may have corresponding pitches such that the helical grooves define one or more passages, and preferably a plurality of passages, between the first and second shafts. Each passage may define a transverse axis extending transversely to the first longitudinal axis, preferably extending substantially vertically. In an exemplary embodiment, the helical groove in each first shaft may extend clockwise from the first end to the second end of the first shaft, and the helical groove in each second shaft may extend counterclockwise from the first end to the second end of the second shaft. In addition or alternatively, the helical groove in each first shaft may define a first pitch, and the helical groove in each second shaft may define a second pitch that is an integer multiple of the first pitch. In a preferred embodiment, the integer is one such that the second pitch equals the first pitch.

A drive mechanism may be coupled to the shafts for rotating the shafts, preferably such that the passages move from the first ends towards the second ends of the shafts for carrying a medical cartridge in each passage between the first and second ends while maintaining the medical cartridge substantially parallel to the transverse axis. In one embodiment, the drive mechanism may include a servomotor coupled to each of the shafts, and/or a controller for synchronizing rotation of the shafts.

In addition, the apparatus may include a track adjacent the first ends of the shafts. The track may include a slot, e.g., between two rails, for guiding medical cartridges into the one or more passages at the first ends of the shafts. The track may be inclined downwardly towards the first ends of the shafts, whereby a medical cartridge carried in the slot may slide automatically into a passage appearing at the first ends of the shafts.

In addition, the apparatus may include a carrier defining a second longitudinal axis that intersects the first longitudinal axis at a convergence region. The carrier may include a plurality of pockets spaced apart a predetermined distance corresponding to an axial spacing of the passages defined by the first and second shafts. In one embodiment, each pocket may be formed in a manifold connected to an endless loop that may extend around and between a plurality of wheels, thereby defining an orbital path. Each pocket is configured for carrying a cartridge adapter therein such that the adapter extends substantially parallel to the transverse axis. Preferably, the second longitudinal axis may be substantially horizontal, and the first longitudinal axis may overlie the second longitudinal axis, thereby defining a vertical angle with the second longitudinal axis that is greater than zero degrees.

A controller may be coupled to the carrier, e.g., to a motor driving the endless loop, for controlling movement of the carrier such that each passage overlies a corresponding pocket as the passage and corresponding pocket approach the convergence region.

In accordance with another aspect of the present invention, a method is provided for assembling an injection device using an assembly apparatus including a plurality of shafts spaced apart from one another and including axes that extend substantially parallel to a first longitudinal axis, such as the apparatus described above. The shafts include helical grooves therein such that the shafts define passages extending transversely with respect to the first longitudinal axis between the first longitudinal axis.

The shafts may be rotated about the their axes such that the passages move along the first longitudinal between first and second ends of the shafts. Syringes or other medical cartridges may be directed in a substantially vertical orientation towards the first ends of the shafts, whereby the syringes may be carried by successive passages from the first ends towards the second ends of the shafts while maintaining the syringes substantially parallel to the transverse axis. Simultaneously, guards or other adapters may be carried along a second longitudinal axis that converges with the first longitudinal axis at a convergence region. The guards may be disposed substantially parallel to the transverse axis and spaced apart such that the guards are aligned with corresponding syringes.

As the syringes and guards move into the convergence region, the syringes may be received in corresponding guards. The syringes may be released from the passages at the second ends of the shafts, whereupon the syringes may drop any remaining distance into the corresponding guards. If necessary, a force may be applied between the syringes and the corresponding guards to engage the syringes with detents on the corresponding guards, and thereby secure the syringes within the corresponding guards.

Other objects and features of the present invention will become apparent from consideration of the following description taken in conjunction with the accompanying drawings.

DETAILED DESCRIPTION OF THE PREFERRED EMBODIMENTS

Turning now to the drawings, FIGS. 1–9 show a preferred embodiment of an apparatus 110 for assembling an injection device 8, including a syringe 90 and a guard 10 for receiving the syringe 90 therein. Generally, the apparatus 110 includes a syringe feed apparatus 120 for maintaining syringes 90 in a desired orientation and spacing, and a guard carrier assembly 210 for maintaining guards 10 in a desired orientation and spacing corresponding to that of the syringes 90. The apparatus 110 also may include a controller 190 (shown in FIG. 5) for synchronizing or otherwise controlling operation of the apparatus 110.

In addition, the apparatus 110 may include accessories for storing and/or guiding the syringes 90 and/or guards 10 before or after assembly into injection devices 8. For example, a first track assembly 200 may be provided for feeding syringes 90 into the syringe feed apparatus 120, and/or a second track assembly 230 may be provided for storing guards 10 before they are loaded onto the guard carrier assembly 210, as described further below.

Figure 2:
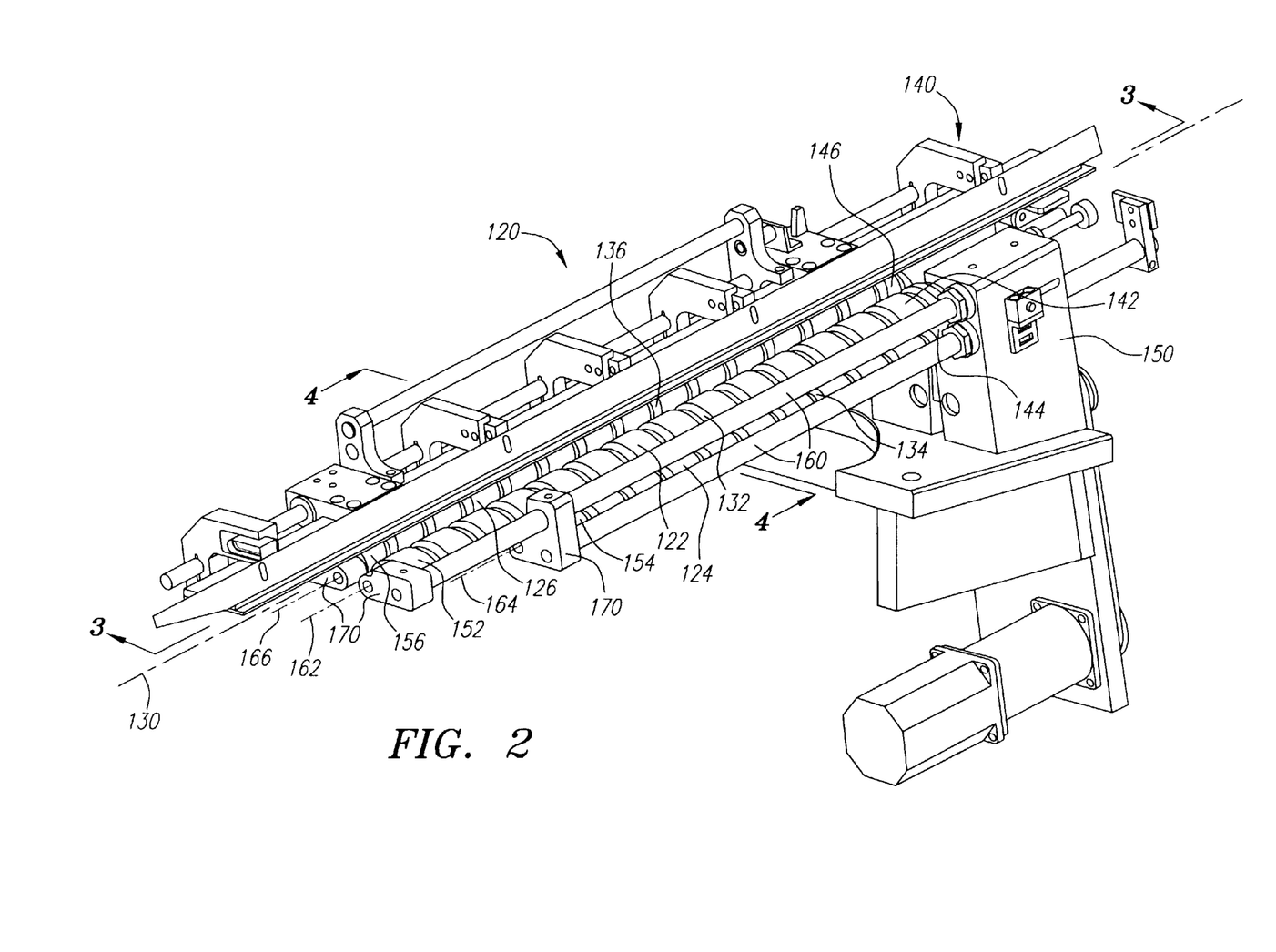
FIG. 2 is a perspective view of the syringe feed apparatus of FIG. 1.
Figure 3:
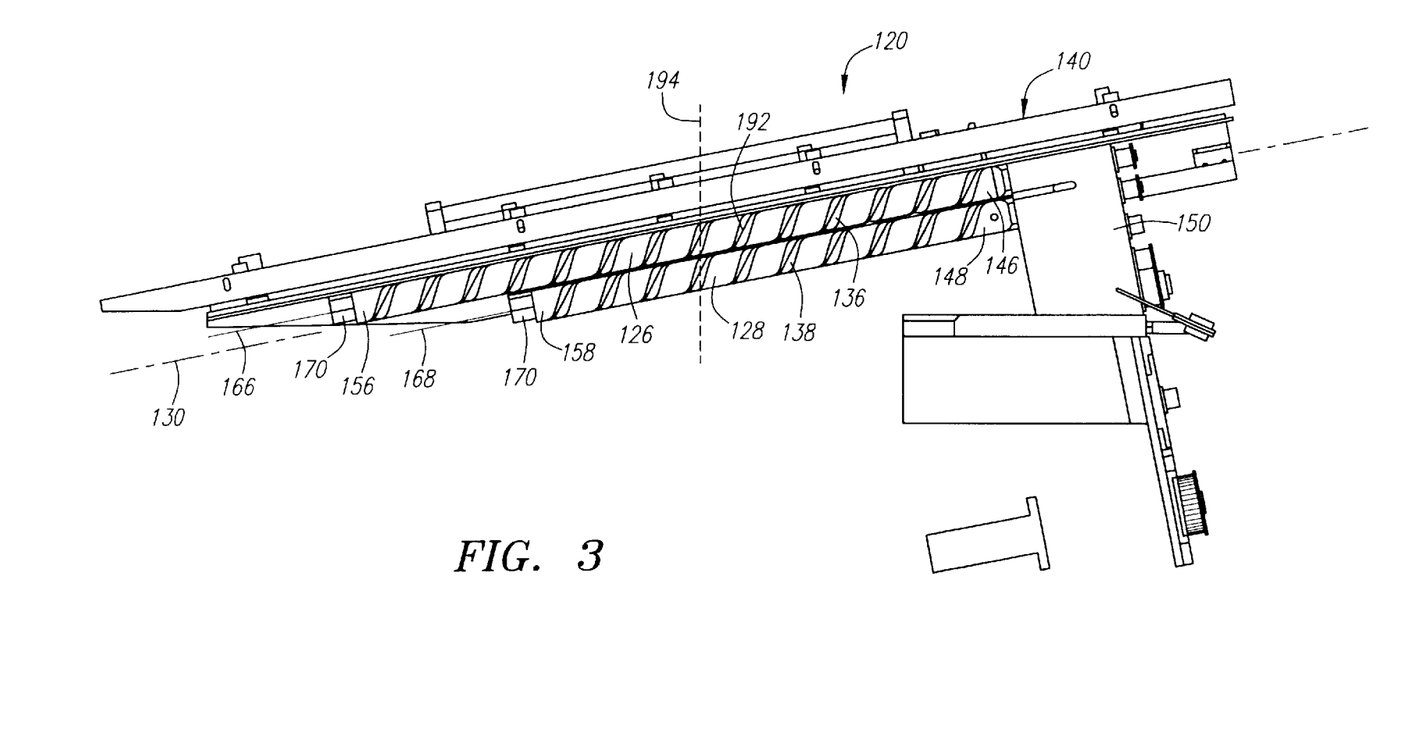
FIG. 3 is a cross-sectional side view of the syringe feed apparatus of FIG. 2 taken along line 3—3.
Figure 4:
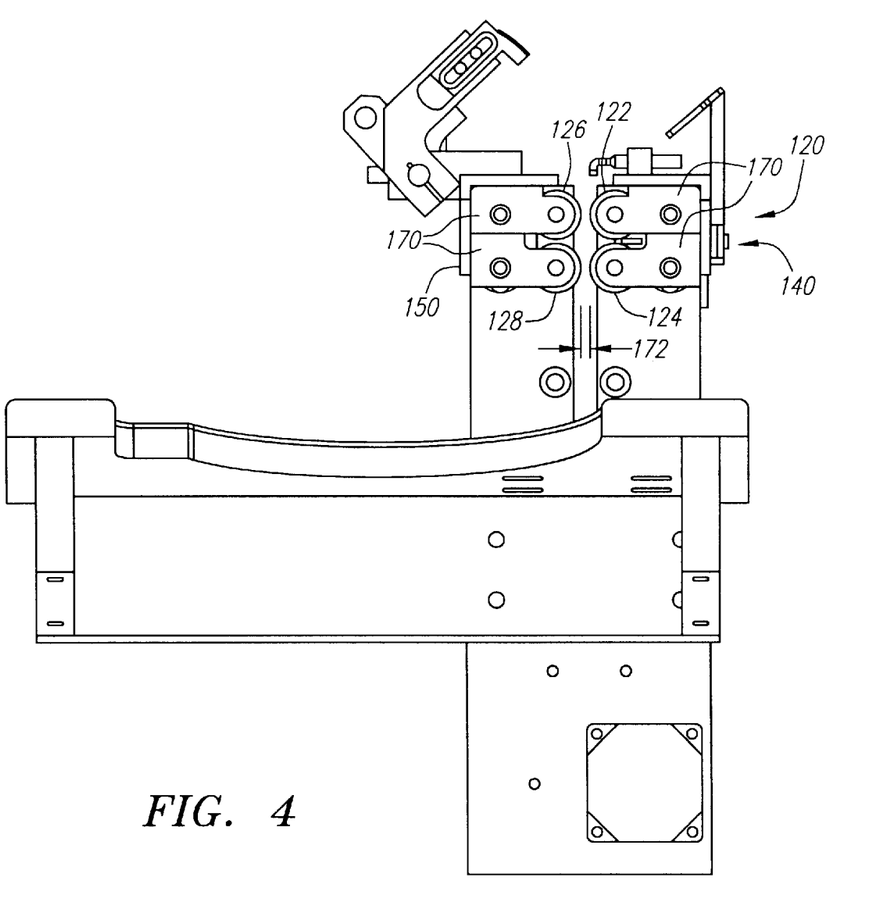
FIG. 4 is a cross-sectional view of the syringe feed apparatus of FIG. 2 taken along line 4—4.

With particular reference to FIGS. 2–4, the syringe feed apparatus 120 generally includes a pair of first shafts 122, 124 and a pair of second shafts 126, 128 spaced apart from one another and extending substantially parallel to a longitudinal axis 130. Each of the shafts 122–128 is a substantially rigid elongate rod or tube including a helical groove 132–138 that extends between a first end 142–148 and a second end 152–158 of the respective shaft 122–128. The shafts 122–128 may have diameters between about fifteen to thirty millimeters (about 1530 mm), and lengths between about fifty and seventy five centimeters (about 50–75 cm), and may be made of conventional materials, such as stainless steel, aluminum, and the like.

Preferably, the grooves 132–138 have substantially constant pitches, e.g., between about one turn every one inch (about one turn every twenty five millimeters) and about one turn every two inches (about one turn every fifty millimeters), and more preferably the pitches of the grooves 132–138 are substantially the same as one another. Alternatively, multiple grooves may be provided in one or more of the screws(not shown) and/or the pitches of the grooves may vary between the screws, although this may complicate synchronizing rotation of the screws.

In one embodiment, the groove 132, 134 in the first shafts 122, 124 may extend clockwise from the first end 142, 144 to a second end 152, 154 of the first shafts 122, 124. Conversely, the groove 136, 138 in the second shafts 126, 128 may extend counterclockwise from the first end 146, 148 to the second end 156, 158 of the second shafts 126, 128. Alternatively, the grooves 132–138 in the first and second shafts 122–128 may extend helically in the same direction, i.e., clockwise or counterclockwise between the first ends 142–148 and the second ends 152–158.

Figure 6:
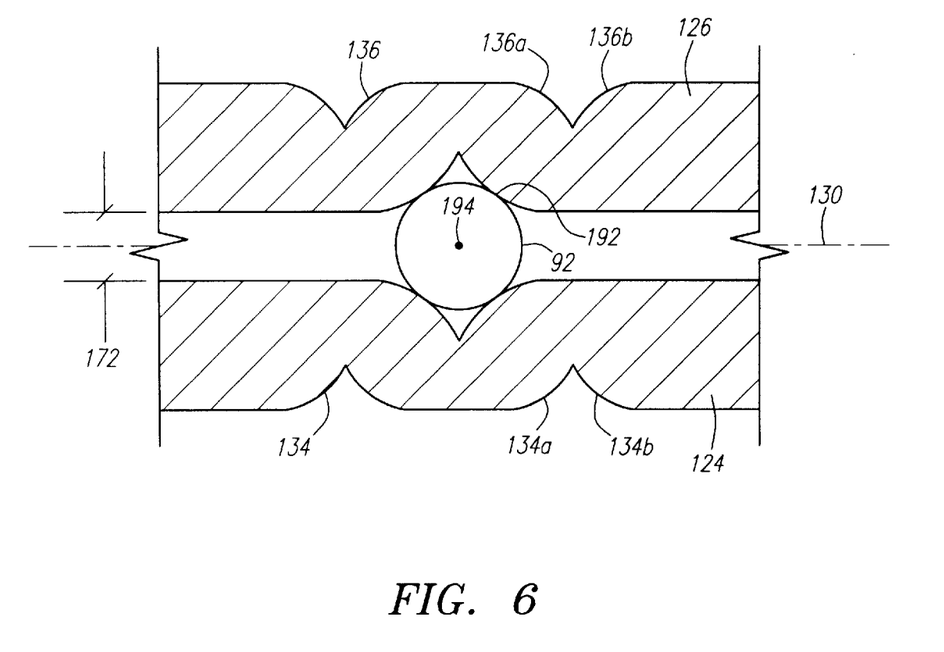
FIG. 6 is a longitudinal cross-section of portions of a pair of shafts of the syringe feed apparatus of FIG. 2, showing grooves that together define a passage extending transversely from a longitudinal axis of the syringe feed apparatus.
Figure 7:
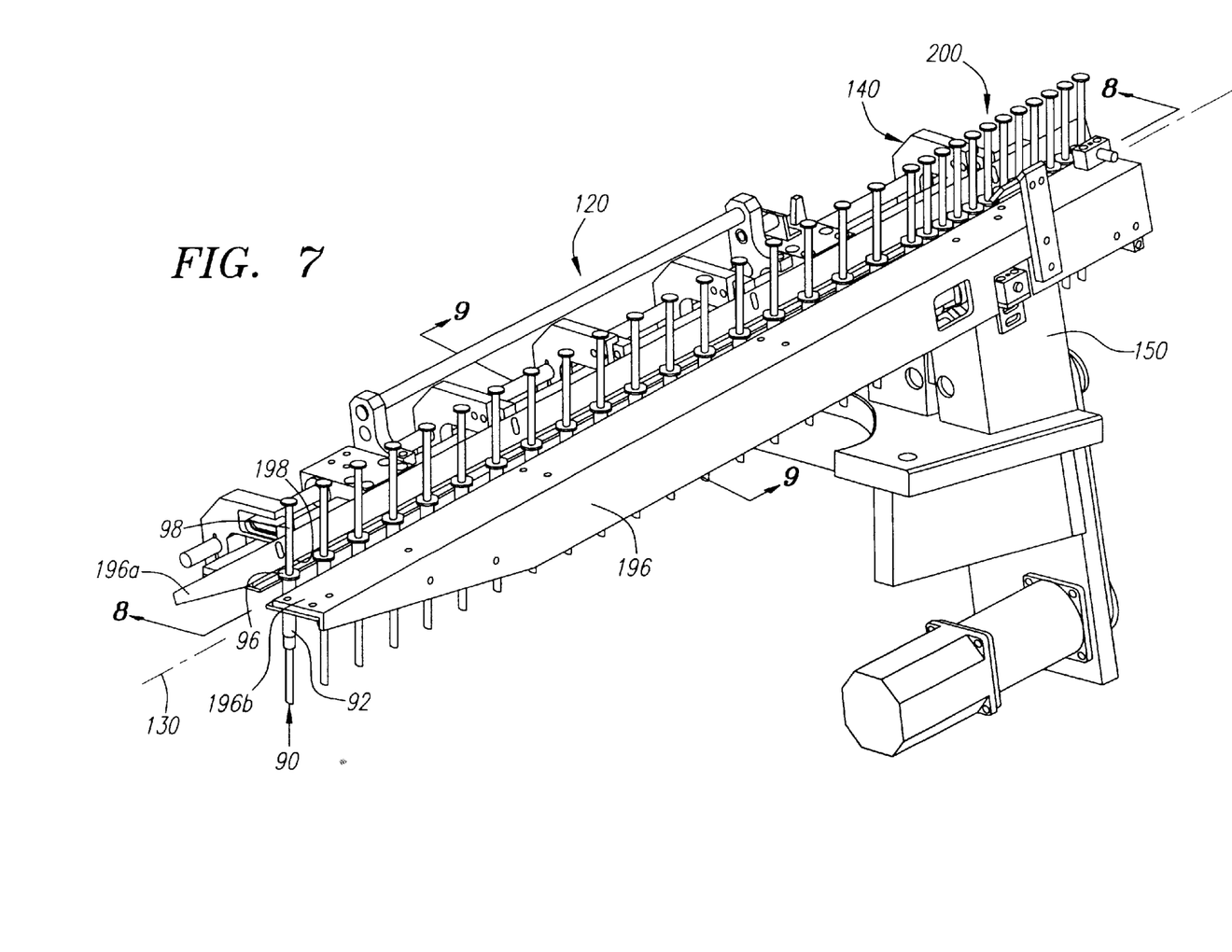
FIG. 7 is a perspective view of the syringe feed apparatus of FIG. 2 carrying a plurality of syringes.
Figure 8:
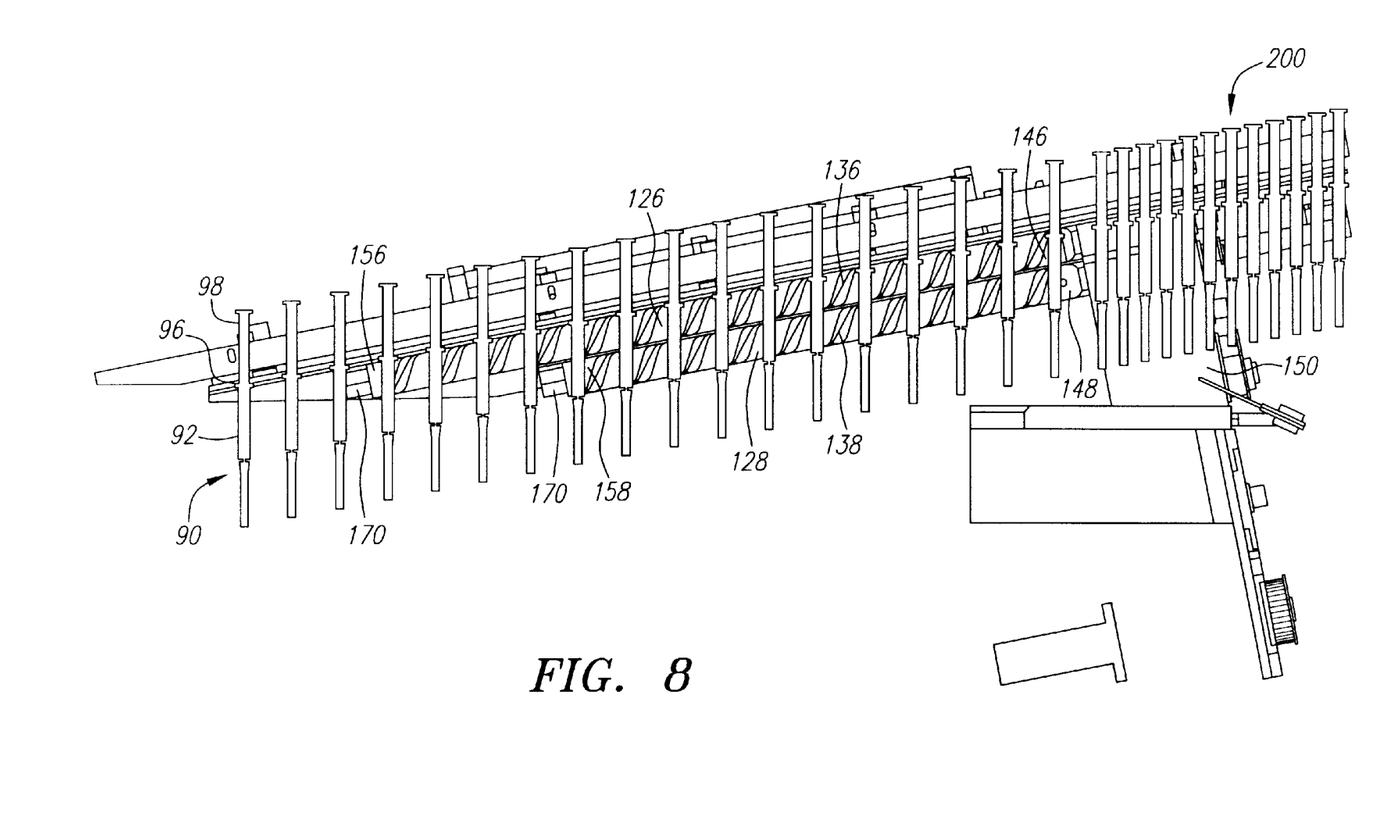
FIG. 8 is a cross-sectional side view of the syringe feed apparatus of FIG. 7 taken along line 8—8.
Figure 9:
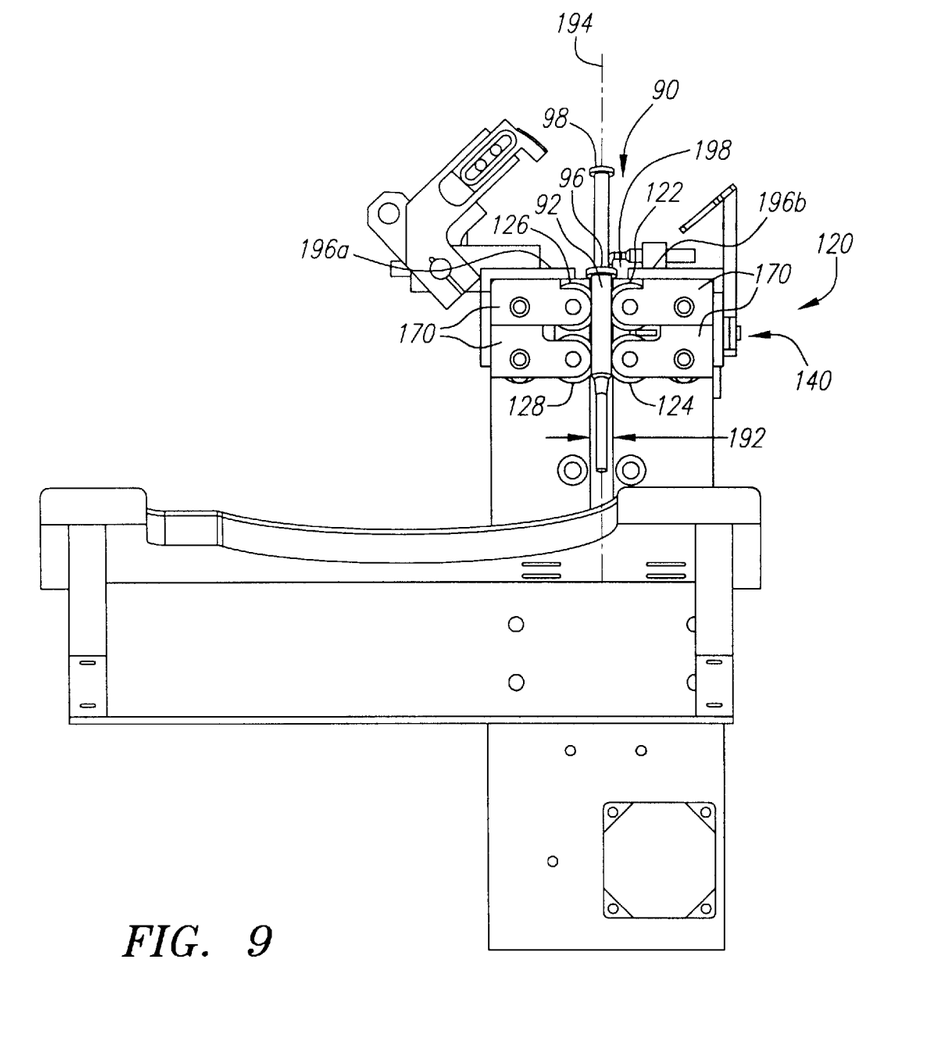
FIG. 9 is a cross-sectional view of the syringe feed apparatus of FIG. 7 taken along line 9—9.

As shown in FIG. 6, the grooves 134, 136 of the shafts 124, 126 (grooves in the other shafts, not shown, may be similar) may have a generally "V" shaped cross-section, thereby defining a leading edge 132a, 136a and a trailing edge 132b, 136b. The leading and trailing edges 132a–136b may be substantially straight or may be concave or convex (not shown). For example, the grooves 132, 136 may have a width "w" of between about eight and twenty two millimeters (about 8–22 mm) and a depth "d" of between about two and twelve millimeters (about 2–12 mm), thereby defining an inclusive angle between them. In a preferred embodiment, the inclusive angle may be about one hundred twenty degrees (120°). Alternatively, other cross-sections, e.g., hemispherical or concave cross-sections (not shown), may be provided that allow a barrel 92 of a syringe 90 to be received and/or engaged within the grooves 132, 136, as shown in FIGS. 7–9. "V" shaped grooves 132, 136, however, may be particularly advantageous for securely carrying a syringe 90 between the shafts 132, 136 while maintaining the syringe 90 in a desired orientation.

A frame 140 may support the shafts 122–128 relative to one another, e.g., to prevent spatial displacement, yet allow the shafts 122–128 to rotate freely about central axes 162–168 that extend substantially parallel to the first longitudinal axis 130. Thus, the frame 140 may maintain the shafts 122–128 spaced apart from one another such that a vertical gap 172 is provided between the first and second shafts 122–128, as best seen in FIG. 4. Preferably, the first and second shafts 122–128 are spaced apart such that the gap 172 is smaller than a cross-section of a barrel 92 of a syringe 90 that may be fed through the feed apparatus 120, as shown in FIGS. 4 and 9. For example, the central axes 162–168 of the first shafts 122, 124 and the second shafts 126, 128 may be spaced apart such that the vertical gap 172 has a width of between about one and twenty millimeters (about 1–20 mm).

Returning to FIGS. 2–4, the frame 140 may include a housing 150 for engaging the first ends 142–148 of the shafts 122–128, and a plurality of longitudinal arms 160 extending from the housing 150 to support brackets 170 for engaging the second ends 152–158 of the shafts 122–128. The ends of the shafts 122–128 may include hubs that may be received in sockets (not shown) in the housing 150 and/or the brackets 170. The housing 150 and/or brackets 170 may also include bearings (also not shown) for facilitating rotation of the shafts 122–128. Alternatively, the ends of the shafts 122–128 may include sockets into which hubs (not shown) from the housing 150 and/or the brackets 170 may be received.

Turning to FIG. 6, the housing 150 may also include a drive mechanism 180 therein that may be coupled to the first and second shafts 122–128 for rotating the first and second shafts about their central axes 162–168. In a preferred embodiment, the drive mechanism 180 includes a plurality of servomotors 182–188 coupled to respective shafts 122–128 for rotating the shafts 122–128 about the axes 162–138. The first end 142–148 of each shaft 122–128 may be directly coupled to a corresponding servomotor 182–188, e.g., by hubs (not shown) extending from the first ends 142–148 into the housing 150. Alternatively, the drive mechanism 180 may include one or more motors (not shown) directly or indirectly coupled to the shafts 122–128, e.g., by gears or belts (also not shown), as is well known to those skilled in the art.

A controller 190, e.g., a computer, may be electrically coupled to the servomotors 182–188 for synchronizing or otherwise controlling rotation of the shafts 122–128. Preferably, the controller 190 synchronizes the servomotors 182–188 to rotate the shafts 122–128 such that the grooves 132–138 define a plurality of passages 192 that extend between the first shafts 122, 124 and the second shafts 126, 128. As the shafts 122–128 are rotated, the passages 192 may move axially from the first ends 142–148 towards the second ends 152–158 of the shafts 122–128.

Preferably, the passages 192 have a cross-section defining a transverse axis 194 that extends transversely with respect to the first longitudinal axis 130, and more preferably that extends substantially vertically. The passages 192 may have a cross-section such that the passages 192 may carry syringes 90 between the first and second shafts 122–128 from their first ends 142–148 towards their second ends 152–158 while maintaining the syringes substantially vertically, as best seen in FIGS. 8 and 9.

Returning to FIGS. 2–4, the pairs of first and second shafts 122–128 include upper shafts 122, 126 and lower shafts 124, 128 that are disposed below the upper shafts 122, 126 of the respective pair. Preferably, the upper shafts 122, 126 and the lower shafts 124, 128 are aligned vertically with one another and have similar diameters such that the gap 172 between the first and second shafts 122–128 is substantially vertical, as best seen in FIG. 4.

In a preferred embodiment, the lower shafts 124, 128 are substantially shorter than the upper shafts 122, 126, as best seen in FIGS. 2 and 3. With the first ends 142–148 of the shafts 122–128 disposed adjacent one another, the second ends 154, 158 of the lower shafts 124, 128 are disposed adjacent an intermediate region of the upper shafts 122, 126. This configuration may be useful for providing the syringes 90 some limited lateral movement as they are received in corresponding guards 10 and/or to provide clearance with other equipment, such as the guard carrier assembly 210, as described further below. Alternatively, the shafts 122–128 may all have lengths that are substantially similar to one another (not shown). In a further alternative, one or more shafts may be eliminated, e.g., one or both lower shafts 124, 128, although the lower shafts 124, 128 may enhance the stability of syringes 90 held within the passages 192 between the shafts 122–128.

With particular reference to FIGS. 7 and 9, the syringe feed apparatus 120 may also include a cover 196 that may be secured to the frame 140. The cover 196 may include panels 196a, 196b that are disposed over the upper shafts 124, 126. Preferably, the panels 196a, 196b are spaced apart from one another such that they define a slot 198 that extends substantially parallel to the longitudinal axis 130. The slot 198 may have a width that is greater than the gap 172 between the shafts 122–128, and preferably that is larger than a cross-section of the passages 192 defined by the grooves 132–138 such that flanges 92 on syringes 90 carried by the shafts 122–128 may pass freely between the panels 196a, 196b, as best seen in FIG. 9.

Alternatively, the slot may have a width that is larger than barrels 92 of syringes 90, yet smaller than flanges 96 on the barrels 92. Such a narrower slot may support the syringes 90 by the flanges 96 for preventing the syringes 90 from falling between the shafts 122–128. In a further alternative, the cover 196 may be eliminated if there are no concerns about accessing the shafts 122–128.

Figure 1:
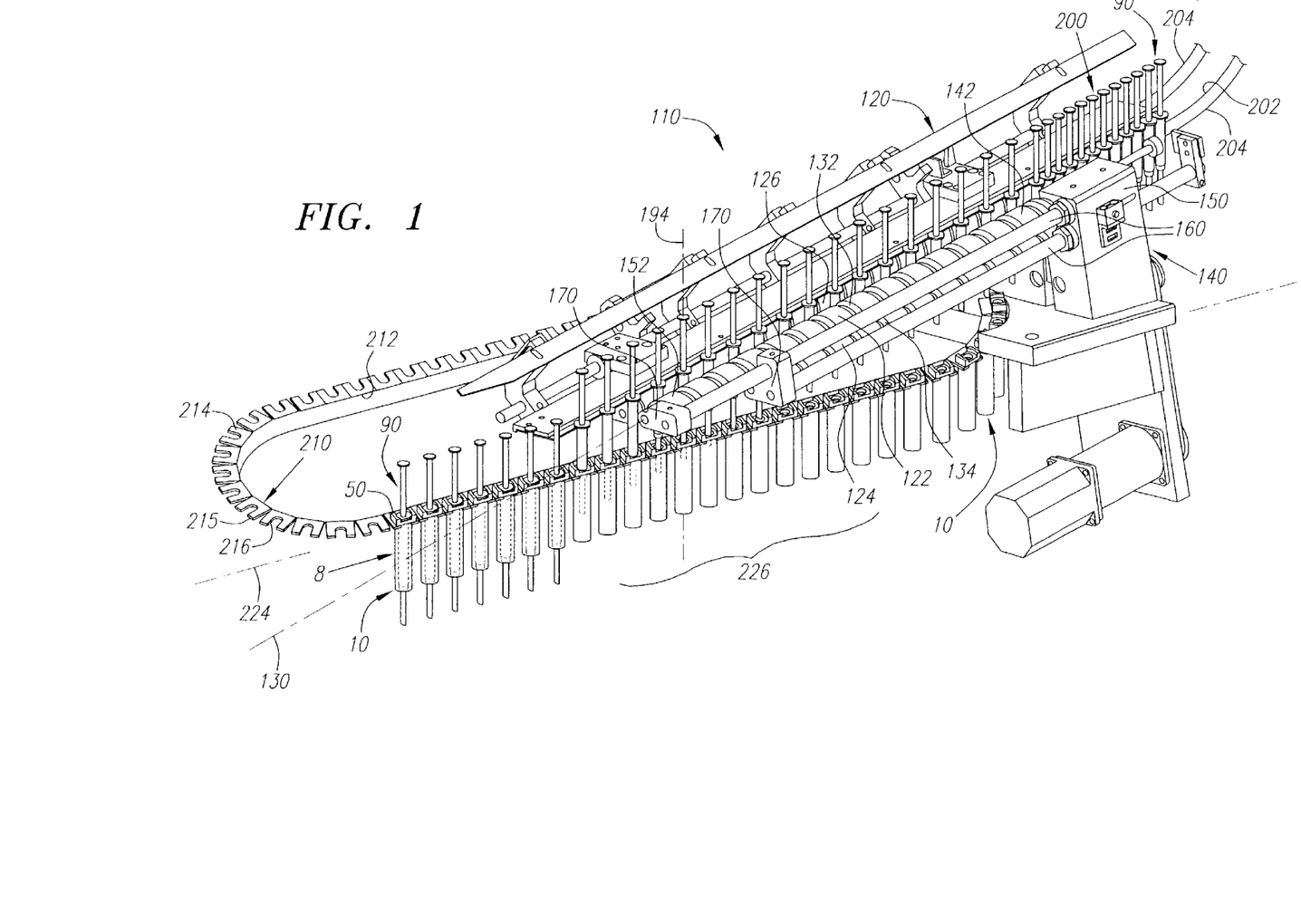
FIG. 1 is a perspective view of an apparatus for assembling injection devices, including a syringe feed apparatus and a guard carrier assembly, in accordance with the present invention.

In addition, as shown in FIGS. 1, 7, and 8, a first track assembly 200 may be provided adjacent the syringe feed apparatus 120, e.g., adjacent the housing 140 and/or the first ends 142–148 of the shafts 122–128. The track assembly 200 may include a slot 202 therein that is aligned with the first longitudinal axis 130, at least where the slot 202 terminates. The slot 202 may have a width larger than barrels 92 of syringes 90, and less than flanges 96 on the syringes 90. Thus, the slot 202 may receive the barrels 92 therein, while preventing the flanges 96 on the syringes 90 from passing through the slot 202, thereby carrying the syringes 90 along the track assembly 200 by the flanges 96.

The track assembly 200 may be substantially straight, e.g., extending substantially parallel to the first longitudinal axis 130, or the track assembly 200 may curve as it extends further away from the first ends 142–148 of the shafts 122–128. In addition, the track assembly 200 may be inclined downwardly towards the first ends 142–148 of the shafts 122–128 and/or disposed generally parallel to the longitudinal axis 130 for allowing syringes 90 to slide freely along the slot 202 between the rails 204.

A portion of the slot 202 in the track assembly 200 may be defined by the cover 196. In addition or alternatively, the track assembly 200 may include one or more pairs of rails 204. Additional pairs of rails (not shown) may be abutted or otherwise connected sequentially to one another in order to connect the syringe feed apparatus 120 with other apparatus. For example, the track assembly 200 may be connected to other components of an assembly line, e.g., a filling line (not shown) that may be used to fill the barrels 92 of the syringes 90 with a desired medication, and/or an apparatus for inserting plungers 98 into the syringes 90, as is well known to those skilled in the art.

The rails 204 may be substantially smooth-walled rods, plates, and the like such that friction resulting from contact between the rails 204 and the flanges 96 on the syringes 90 may be substantially minimized to allow the syringes 90 to slide freely towards the first ends 142–148 of the shafts 122–128 under gravity. Alternatively, the syringes 90 may be pushed along the track assembly 200, e.g., as additional syringes (not shown) are loaded onto the track assembly 200. In a further alternative, the track assembly 200 may include a mechanism, such as a belt drive (not shown), for advancing the syringes 90 along the slot 202 towards the first ends 142–148 of the shafts 122–128 at a predetermined speed and biasing the syringes 90 to enter the passages 192 as they become available, as described further below.

Figure 5:
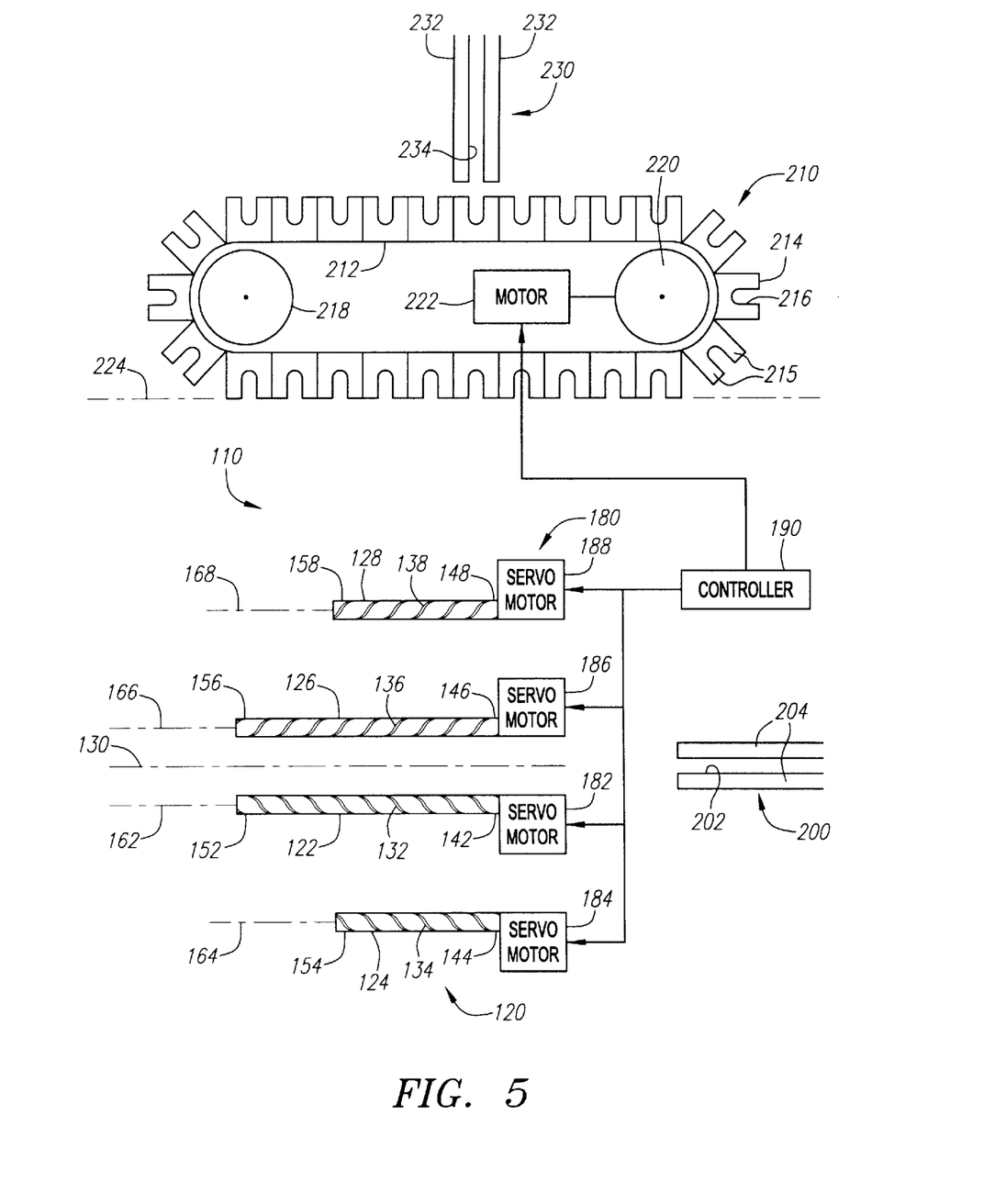
FIG. 5 is a schematic of a system for controlling operation of the apparatus of FIG. 1.

Turning to FIGS. 1, 5, and 10, the guard carrier assembly 210 may be an endless loop 212 including a plurality of manifolds 214 including pockets 216 for receiving guards 10 or other adapters therein. For example, the endless loop 212 may include a belt or chain drive that travels in an orbital path between one or more wheels, such as the pair of wheels 218, 220 shown in FIG. 5. At least one of the wheels 218 may be driven by a motor 222, which may be operated to rotate the wheel 218, and consequently move the endless loop 212 in the orbital path around the wheels 218, 220. The endless loop 212 may be coupled to the wheel 218 by sprockets (not shown) and/or by friction, thereby ensuring that the endless loop 212 moves in synchronization with the wheel 218.

The manifolds 214 may be secured to the endless loop 212 such that the manifolds 214 remain at a predetermined spacing from one another as the manifolds 214 travel around the orbital path. Preferably, the endless loop 212 defines a second longitudinal axis 224 that may be aligned with the first longitudinal axis 130 of the syringe feed apparatus 120, e.g., such that the first and second longitudinal axes 130, 224 converge at a convergence region 226. More preferably, the second longitudinal axis 220 is substantially horizontal and intersects the first longitudinal axis 130 within the convergence region 226.

The manifolds 214 may be spaced apart such that, as the manifolds 214 travel along the portion of the orbital path defining the second longitudinal axis 220, the pockets 216 in the manifolds 214 may be aligned with the transverse axes 194 of respective passages 192 extending through the first and second shafts 122–128 of the syringe feed apparatus 120. Preferably, with the transverse axes 194 being substantially vertical, the pockets 216 are disposed substantially vertically below respective passages 192 as the pockets 216 approach the convergence region 226, as best seen in FIG. 1. Thus, the spacing of the manifolds 214 may correspond to the pitch of the grooves 132–138 in the shafts 122–128 as projected onto the second longitudinal axis 224.

The manifolds 214 may be "C" shaped bodies that include opposing flanges 215 defining the pockets 216 therebetween. The pockets 216 may be sufficiently large to receive a portion of a guard 10 therethrough, yet small enough to prevent a finger grip 50 on the guard 10 from passing between the flanges 215. Thus, the guard 10 may be suspended from the manifold 214 by the finger grip 50, e.g., such that the guard 10 extends substantially vertically.

With particular reference to FIG. 5, a controller, such as the controller 190 used to control the servomotors 181–184, may be coupled to the motor 222 for controlling the speed of the motor 222, and consequently, the speed at which the manifolds 214 move along the second longitudinal axis 224. Thus, the controller 190 may control and coordinate operation of the syringe feed apparatus 120 and the guard carrier assembly 210, to properly align syringes 90 and guards 10 as they are assembled into injection devices 8, as described further below. Alternatively, separate controllers (not shown) may be coupled to the motor 218 of the guard carrier assembly 210 and/or to one or more of the servomotors 182–188 of the syringe feed apparatus 120.

In addition, as shown in FIG. 5, a second track assembly 230 may be provided for guiding guards 10 (not shown in FIG. 5) onto the guard carrier assembly 210. Similar to the first track assembly 200, the second track assembly 230 may include a pair of rails 232 defining a slot 234 therebetween. Preferably, the rails 232 are spaced apart a predetermined distance such that the slot 234 is larger than a portion of the guards 10, yet smaller than the finger grips 50 of the guards 10, similar to the pockets 216 in the manifolds 214.

The second track assembly 230 may be inclined downwardly towards the endless loop 212, such that the guards 10 may freely slide down the rails 232 and onto the manifolds 214. Alternatively, the guards 10 may be directed along the track assembly 230 towards the manifolds 214, e.g., as guards 10 are loaded onto the track assembly 230 and/or by a belt or other mechanism for biasing the guards 10 towards the manifolds 214.

Thus, the lead guard 10 in the second track assembly 230 may be free to slide into the next available pocket 216 as the manifolds 214 move along the orbital path. Optionally, a shuttle arm (not shown) may be used to guide the guards 10 into the available pockets 216 as the endless loop 212 moves around the orbital path and/or prevent multiple guards from trying to enter a single pocket 216. Such a shuttle arm may reduce the risk of a guard 10 being misaligned or jammed as it is loaded onto the guard carrier assembly 210, thereby allowing higher speeds to be used to load the guards 10 onto the guard carrier assembly 210.

Returning to FIGS. 1 and 7–9, the apparatus 110 may be used to assemble syringes 90 and guards 10 into ready-to-use injection devices 8. The syringes 90 may be pre-filled syringes or user-filled syringes. Alternatively, the feed apparatus 120 may be used carry other medical cartridges, such as ampoules that may or may not have their own needles (not shown). The guards 10 carried by the carrier assembly 210 may be manual guards, such as those disclosed in U.S. Pat. Nos. 6,030,366, 6,159,183, and 6,171,283, the disclosures of which are expressly incorporated herein by reference. Alternatively, the guards 10 may be automatic or "passive" guards, such as those disclosed in copending application Ser. No. 09/566,224, filed May 5, 2000, and Ser. No. 09/724,657, filed Nov. 11, 2000, the disclosures of which are also expressly incorporated herein by reference. In a further alternative, the guards 10 may be replaced with cartridge holders that may or may not include a shield device, such as those disclosed in U.S. Pat. Nos. 5,437,647 and 5,624,400, the disclosures of which are also expressly incorporated herein by reference.

A plurality of syringes 90 may be loaded onto the first track assembly 200, e.g., from a filling line and/or other manufacturing equipment (not shown). The first track assembly 200 may guide and/or direct the syringes 90 towards the first ends 142–148 of the shafts 122–128. As the shafts 122–128 rotate, the grooves 132–138 move until a passage 192 is created at the first ends 142–148 of the shafts 122–128. The lead syringe 90 may then be picked up and carried within the passage 192 as the shafts 122–128 continue to rotate, thereby directing the syringe 90 along the first longitudinal axis 130 towards the second ends 152–158 of the shafts 122–128. Subsequently, another passage 192 may be created, and the next syringe 90 may also be carried along between the shafts 122–128. Because of the precise spacing of the shafts 122–128 and the configuration of the grooves 132–138, a plurality of syringes 90 may be securely carried and lowered towards the convergence region 226, while maintaining the syringes 90 substantially vertically. The number of syringes 90 may match the number of turns of the grooves 132–138 in the shafts 122–128.

Simultaneously, a plurality of guards 10 may be loaded onto the second track assembly 230, e.g., from a manufacturing line and/or storage area (not shown). The second track assembly 230 may guide and/or direct the guards 10 towards the guard carrier assembly 210 until the guards 10 are received in sequential pockets 216 of manifolds 214 moving along the orbital path. If desired, a shuttle arm or other device (not shown) may positively grab a lead guard 10,e.g., by its finger flange 50, insert it into the available pocket 216, and then release the guard 10 in the pocket 216. Because the manifolds 214 may be moving continuously at relatively high speed, the shuttle arm may move laterally to direct the lead guard 10 into the corresponding pocket 216 and/or the flanges 215 of the manifolds 214 may include tapered edges (not shown) to facilitate inserting the guard 10.

As the manifolds 214 move along the orbital path from the second track assembly 230, the guards 10 may be directed along the second longitudinal axis 224 towards the convergence zone 226. Because the movement of the manifolds 214 is synchronized with the rotation of the shafts 122–128, the guards 10 may be aligned with the syringes 90, preferably such that the guards 10 travel substantially vertically below corresponding syringes 90. Thus, as the guards 10 and syringes 90 move into the convergence zone, the syringes 90 may be lowered into the corresponding guards 10. Once the syringes 90 reach the second ends 152–158 of the shafts 122–128, e.g., at the end of the convergence zone 226 (see FIG. 1), the syringes 90 may be released, causing the syringes 90 to drop any remaining distance into the corresponding guards 10.

In a preferred embodiment, the guards 10 may include detents (not shown) for engaging the syringes 90 to lock or substantially permanently encapsulate the syringes 90 into the guards 10. To assist in engaging the syringes 90 with the detents, the guard carrier assembly 230 may include a device (not shown) for directing the syringes 90 and the guards 10 together. For example, a tapper mechanism (not shown) may apply a vertically downward force on the flanges 96 of the sequential syringes 90, thereby causing detents on the corresponding guards 10 to deflect sufficiently to accommodate inserting the flanges 96 beyond the detents, whereupon the detents may engage the flanges 96 to secure the syringes 90 into the guards 10. Thus, the tapper mechanism may automatically lock the syringes 90 into the guards 10 to provide injection devices 8, thereby eliminating the need to manually assemble the injection devices 8, as explained in the patents incorporated by reference above.

In addition, the guard carrier assembly 210 may include quality control devices (not shown) for automatically monitoring the injection devices 8 to ensure that they are properly assembled. Finally, the guard carrier assembly 210 may include one or more ejector mechanisms (not shown) for ejecting the assembled injection devices 8 from the manifolds 214. For example, horizontal arms (not shown) may be provided for pushing the injection devices 8 out of the pockets 216, e.g., into bins or onto other devices, e.g., for packaging, sterilization, and/or other final manufacturing steps, as are well know to those skilled in the art.

Thus, an assembly apparatus in accordance with the present invention may provide injection devices 8 that may be shipped to users ready for use. The users need merely remove an injection device from packaging (if packaged), remove a needle cap, make an injection, and activate the shield (if provided on the guard) either manually or automatically upon completing the injection. Extra handling of the syringes and guards by end-users before making an injection may be eliminated, thereby ensuring that the injection devices are properly assembled and prepared before use. The apparatus may allow injection devices to be assembled at high speeds, for example, as fast as three hundred (300) devices per minute with substantial accuracy and consistency.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for assembling an injection device including a medical cartridge and an adapter comprising a body for receiving the medical cartridge in an open end thereof, comprising:

a pair of first shafts disposed adjacent one another, each first shaft comprising a helical groove therein extending from a first end to a second end of the first shaft;

one or more second shafts spaced apart a predetermined distance from the pair of first shafts, the first and second shafts extending substantially parallel to a first longitudinal axis, each second shaft comprising a helical groove therein extending from a first end to a second end of the second shaft, the helical grooves in the first and second shafts having corresponding pitches such that the helical grooves define one or more passages between the first and second shafts that define a transverse axis extending transversely to the first longitudinal axis; and a drive mechanism coupled to the first and second shafts for rotating the first and second shafts such that each passage moves from the first ends towards the second ends of the first and second shafts for carrying a medical cartridge in the passage between the first and second ends while maintaining the medical cartridge substantially parallel to the transverse axis.

2. The apparatus of claim 1, wherein:
the helical groove in each first shaft extends clockwise from the first end to the second end of the first shaft; and
the helical groove in each second shaft extends counter-clockwise from the first end to the second end of the second shaft.

3. The apparatus of claim 1, wherein the helical groove in each first shaft defines a first pitch, and wherein the helical groove in each second shaft defines a second pitch that is an integer multiple of the first pitch.

4. The apparatus of claim 3, wherein the second pitch equals the first pitch.

5. The apparatus of claim 1, wherein the transverse axis is substantially vertical.

6. The apparatus of claim 5, wherein the first longitudinal axis is inclined with respect to a horizontal plane.

7. The apparatus of claim 1, wherein the pair of first shafts comprises an upper shaft and a lower shaft disposed below the upper shaft.

8. The apparatus of claim 1, further comprising a track adjacent the first ends of the first and second shafts, the track comprising a slot therein for guiding medical cartridges into the one or more passages at the first ends of the first and second shafts.

9. The apparatus of claim 8, wherein the track is inclined downwardly towards the first ends of the first and second shafts, whereby a medical cartridge carried in the slot may slide automatically into the passage appearing at the first ends of the first and second shafts.

10. The apparatus of claim 1, wherein the helical grooves in the first and second shafts comprise a plurality of turns between the first and second ends, thereby defining a plurality of passages extending between the first and second shafts.

11. The apparatus of claim 10, further comprising:
a carrier defining a second longitudinal axis that converges with the first longitudinal axis at a convergence region, the carrier comprising a plurality of pockets spaced apart a predetermined distance corresponding to an axial spacing of the passages defined by the first and second shafts, each pocket configured for carrying a cartridge adapter therein such that the adapter extends substantially parallel to the transverse axis; and
a controller for controlling movement of the carrier such that each passage overlies a corresponding pocket as the passage and corresponding pocket approach the convergence region for inserting a cartridge carried in the passage into an adapter carried in the corresponding pocket.

12. The apparatus of claim 11, wherein the second longitudinal axis is substantially horizontal, and wherein the first longitudinal axis overlies the second longitudinal axis, thereby defining a vertical angle with the second longitudinal axis that is greater than zero degrees.

13. The apparatus of claim 11, wherein the helical grooves terminate at the second ends of the first and second shafts for releasing cartridges carried in the passages as the cartridges reach the second ends of the first and second shafts.

14. The apparatus of claim 11, further comprising a insertion mechanism adjacent the convergence region for engaging cartridges with detents on adapters into which the cartridges are received at the convergence region.

15. The apparatus of claim 11, further comprising a track disposed adjacent the carrier for guiding adapters into the pockets.

16. An apparatus for assembling an injection device including a syringe and a guard comprising a body for receiving the syringe in an open end of the guard, comprising:
a pair of first shafts disposed one above the other, each first shaft comprising a groove therein extending helically from a first end to a second end of the first shaft;
a pair of second shafts disposed one above the other and spaced apart a predetermined distance from the pair of first shafts, each second shaft comprising a helical groove therein extending helically from a first end to a second end of the second shaft, the first and second shafts extending substantially parallel to a first longitudinal axis that is inclined such that the second ends are lower than the first ends of the first and second shafts, the helical grooves in the first and second shafts having corresponding pitches such that the helical grooves define a plurality of passages extending between the first and second shafts that define a vertical axis; and
a driver coupled to the first and second shafts for rotating the first and second shafts such that the passages may carry syringes between the first and second ends while maintaining the syringes substantially vertically.

17. The apparatus of claim 16, further comprising a carrier assembly defining a horizontal longitudinal axis that intersects the first longitudinal axis at a convergence region, and comprising a plurality of pockets spaced apart a predetermined distance corresponding to an axial spacing of the passages defined by the first and second shafts, the pockets configured for carrying guards therein such that the guards extend substantially vertically; and
a controller for controlling movement of the carrier assembly such that the passages overlie corresponding pockets as the passages and corresponding pockets approach the convergence region for inserting cartridges carried in the passages into the guards carried in the corresponding pockets.

18. The apparatus of claim 16, further comprising an inclined track adjacent the first ends of the first and second shafts, the track comprising a slot having a width for slidably receiving barrels of syringes therein for guiding the syringes into the passages at the first ends of the first and second shafts.

* * * * *